United States Patent [19]

Trill

[11] Patent Number: 4,605,550

[45] Date of Patent: Aug. 12, 1986

[54] DELAYED RELEASE FORMULATIONS AND PROCESSES FOR MAKING THEM

[75] Inventor: Anthony J. Trill, Horsham, England

[73] Assignee: A. H. Robins Company, Inc., Richmond, Va.

[21] Appl. No.: 617,576

[22] Filed: Jun. 5, 1984

[30] Foreign Application Priority Data

Jun. 6, 1983 [GB] United Kingdom ............... 8315476

[51] Int. Cl.$^4$ .................... A61K 9/16; A61K 9/26; A61K 31/78

[52] U.S. Cl. ........................................ 424/22; 424/19; 424/147; 424/81; 71/4; 71/64.11; 71/903; 71/904; 514/502; 514/951

[58] Field of Search ............... 424/19, 22, 147, 81, 424/361; 71/903, 904, 64.11, 4; 514/502, 951

[56] References Cited

U.S. PATENT DOCUMENTS

| | | | |
|---|---|---|---|
| 2,987,445 | 6/1961 | Levesque | 424/81 |
| 3,584,113 | 6/1981 | Takebe et al. | 424/81 |
| 3,584,114 | 6/1981 | Cavalli et al. | 424/147 |
| 3,822,343 | 7/1974 | Hill et al. | 424/147 |
| 3,943,063 | 3/1976 | Morishita et al. | 71/64.11 |
| 4,102,806 | 7/1978 | Kondo et al. | 424/19 |
| 4,341,759 | 7/1982 | Bogentoft et al. | 424/19 |
| 4,499,066 | 2/1985 | Moro et al. | 424/22 |

FOREIGN PATENT DOCUMENTS

EP107107 5/1984 European Pat. Off. ............ 424/22

*Primary Examiner*—Ronald W. Griffin

[57] ABSTRACT

There is disclosed a granular composition having particles of average particle size as determined by sieving in the range 70 to 500 microns, the said particles comprising up to 55% of active ingredient e.g. ferrous sulphate having primary particles the maximum dimension (A) of which as determined by microscopy is less than 50 microns and a particulate water soluble extender e.g. lactose having an average particle size (B) as determined by sieving in excess of 50 microns, the particles of active ingredient and water soluble extender being held in self-supporting spaced relationship by a water insoluble polymer film matrix e.g. of a polyacrylate polymer, providing the balance of the weight of the particle and being less than 50% by weight of the particle.

The invention also extends to a blend convertible by pressure alone to a substantially continuous three-dimensional porous matrix substantially devoid of separate resin particles, of active ingredient/water soluble extender/resin particles, e.g. as above, in which the active ingredient comprises 45 to 60%, the water soluble extender comprises 35 to 45%, and the resin comprises 5 to 15% by weight and a water insoluble extending agent or filler for the matrix resin and a water soluble or insoluble tableting aid or lubricant, the active ingredient/water soluble extender/resin particles comprising 80 to 95%, the water insoluble extending agent or filler for the matrix resin comprising 5 to 15% and the lubricant 0.2 to 5% of the blend.

12 Claims, 25 Drawing Figures

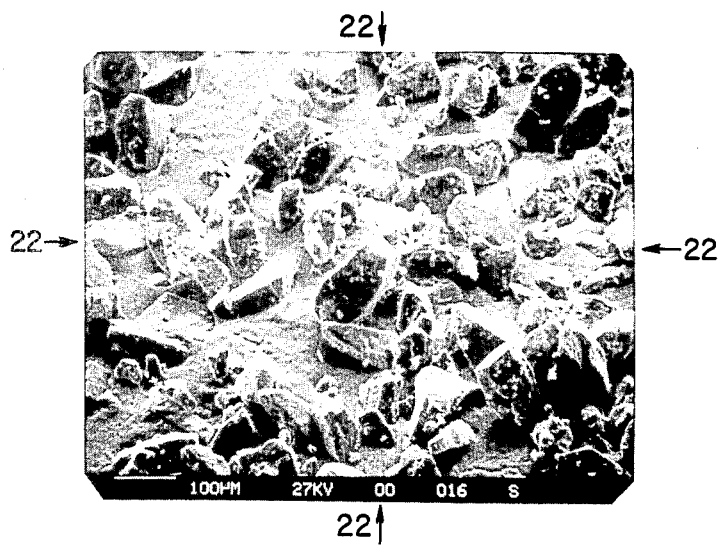
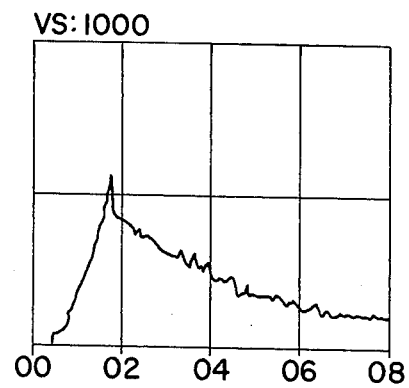
Fig.2
Fig.1
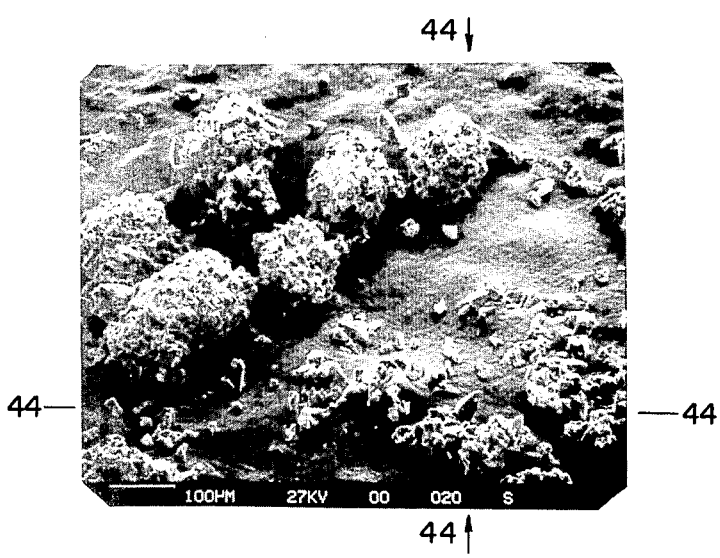
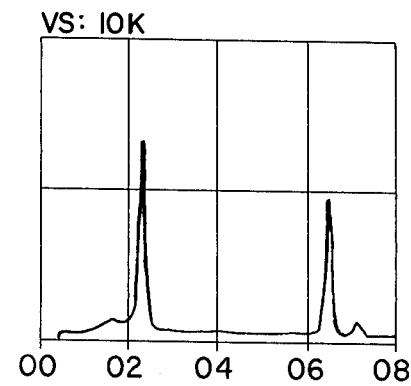
Fig.4
Fig.3

DELAYED RELEASE FORMULATIONS AND PROCESSES FOR MAKING THEM

The present invention relates to controlled or delayed release formulations, processes for making them and novel compositions for use in such processes.

The formulations may contain pharmaceutically active components such as inorganic pharmaceutically active materials for example ferrous sulphate.

Delayed release or controlled release pharmaceutical formulations are known in which the active ingredient is located within a porous resin coating but these materials will not have the benefits of the present tablet formulation in that they will not have a continuous rate of release of the active ingredient because once the active ingredient inside the coating has become significantly dissolved there will be nothing to support the coating and it will tend to collapse inwards or rupture outwardly either of which events will cause the rate of release to suddenly change markedly. Thus in the event of inward collapse the rate at which the active material is released by the formulation will be reduced whilst in the event of rupture of the film wall the rate of release will increase.

With the present invention a substantially constant surface area for dissolution will be exposed throughout because the continuous matrix in the tablet and thus its porous structure will remain substantially constant and the active material being distributed substantially evenly throughout the matrix will remain relatively evenly accessible to the solubilizing liquids throughout the dissolution process.

Eudragit material manufactured by Rhom Pharma GmbH of Darmstadt Germany is a polyacrylate having excellent physiological compatability and desirable toxicological properties.

The material is advocated by the manufacturers for controlled release pharmaceutical formulations but the particular method of making a three-dimensional matrix described herein has not previously been proposed nor have particles of the structure shown herein been proposed with their considerable benefits in ease of conversion into tablets and ease of manufacture in a controlled manner as described above.

Thus according to the present invention there is provided a granular composition having particles of average particle size as determined by sieving in the range 70 to 500 microns e.g. in the range 100 microns to 300 microns comprising up to 55% e.g. 10 to 55 or 45 to 55% of active ingredient having primary particles the maximum dimension (A) of which as determined by microscopy as less than 50 microns and preferably of the order of 10 to 40 microns and a particulate water soluble extender, the water soluble extender preferably being one which is soluble in less than 20 parts of water (BP) and preferably soluble in less than 10 parts of water (BP) whilst being practically insoluble in the solvent used to process the granulate, the water soluble extender having an average particle size (B) as determined by sieving in excess of 50 microns e.g. in the range 50 to 100 microns especially in the range 60 to 80 microns, and preferably the ratio of B:A being in excess of 1:1 especially in excess of 2:1 e.g. at least 2.5:1 or 3:1, the particles of active ingredient and water soluble extender being held in self-supporting spaced relationship by a water insoluble polymer film matrix providing the balance of the weight of the particle and being less than 50% by weight of the particle.

The invention also extends to particles in which 45 to 55% is the active ingredient, 40 to 55% is the water soluble particulate extender and less than 15% is the polymer film matrix.

A further form of the invention comprises a blend, convertible by pressure alone to a substantially continuous three-dimensional porous matrix substantially devoid of separate resin particles, of active ingredient/water soluble extender/resin particles in which the active ingredient comprises 45 to 60% e.g. 48 to 52% or about 50%, the water soluble extender comprises 35 to 45% e.g. 38 to 42% e.g. about 40%, and the resin comprises 5 to 15% e.g. 8 to 12% e.g. 10% by weight and a water insoluble and mineral acid insoluble caking preventing and extending filler or agent e.g. talc for the matrix resin, this filler also helping to prevent caking on standing and a tableting aid or lubricant e.g. magnesium stearate, the active ingredient/water soluble extender/resin particles comprising 80 to 95%, the water insoluble extending filler or agent for the matrix resin comprising 5 to 15% and the lubricant 0.2 to 5% e.g. 3% of the blend.

The invention further extends to a process of forming a slow release tablet which comprises converting a blend in accordance with the invention by pressure alone without the aid of a solvent to tablet form, and to tablets formed by such a process.

In a preferred form of the invention the active ingredient is ferrous sulphate, the water soluble extender is lactose and the polymer is a polyacrylate polymer.

The invention may be put into practice in various ways and one specific embodiment will be described by way of example to illustrate the invention with reference to the following Examples, and the accompanying drawings in which FIGS. 1, 3, 5, 6, 7, 9, 11, 13, 15, 16, 18 and 19 are scanning electron photomicrographs, FIGS. 2, 4, 8, 10, 12, 14, 17, and 22 to 25 are representations of the oscilloscope plots of X-ray emission analyses (EDAX) carried out during the production of the scanning electron photomicrographs and FIGS. 20 and 21 are diagrammatic representations of FIGS. 19 and 18 respectively;

FIG. 1 showing the lactose used in the Example;

FIG. 2 being the EDAX plot carried out at the intersection of arrows 22 in FIG. 1;

FIG. 3 showing the ferrous sulphate used in the Example, the top left-hand corner containing oblate agglomerates typically 125 to 250 microns across, the primary ferrous sulphate particles being in the middle and having particle sizes less than 50 microns;

FIG. 4 being the EDAX plot carried out at the intersection of arrows 44 in FIG. 3 on a primarily ferrous sulphate particle about 30 microns long;

FIG. 5 showing a mixture of small granules of the composition in accordance with the invention (one in the centre) and talc flakes e.g. 50 and being an enlarged view of the view shown in FIG. 6;

FIG. 6 is a view of a larger area to that shown in FIG. 5, the central granule in FIG. 5 being at the intersection of the arrows 61, other granules being marked by the intersection of the arrows 62 and 63 and all giving EDAX plots as in FIG. 8;

FIG. 7 shows a mixture of larger granules on left-hand side and at the top and seven smaller granules at bottom right;

FIG. 8 being an EDAX plot carried out at the intersection of arrows 80 in FIG. 7;

FIG. 9 shows a talc flake located at the intersection of arrows 90 in FIG. 7;

FIG. 10 being an EDAX plot carried out at the intersection of arrows 91 in FIG. 9;

FIG. 11 shows a lactose crystal located at the intersection of arrows 110 in FIG. 7;

FIG. 12 being an EDAX plot carried out at the intersection of arrows 111 in FIG. 11;

FIG. 13 shows an iron sulphate primary crystal located at the intersection of the arrows 130 in FIG. 7;

FIG. 14 being an EDAX plot carried out at the intersection of arrows 131 in FIG. 13;

Figure 7:
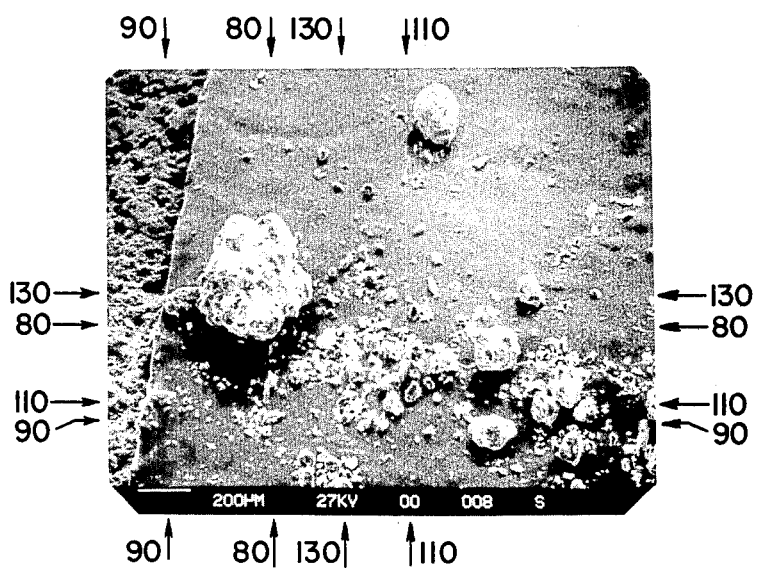
Figure 8:
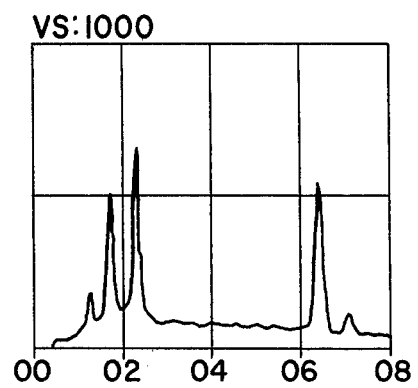
Figure 18:
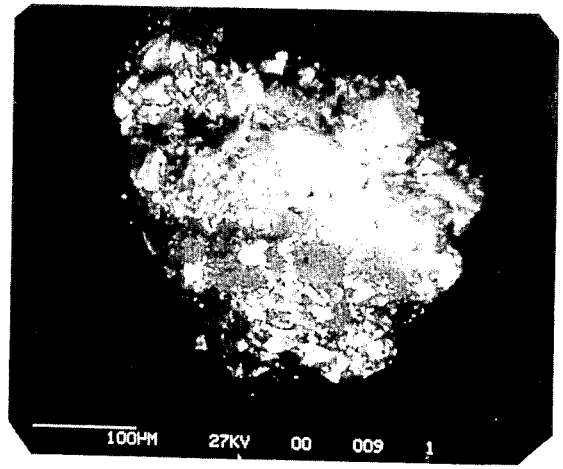
Figure 19:
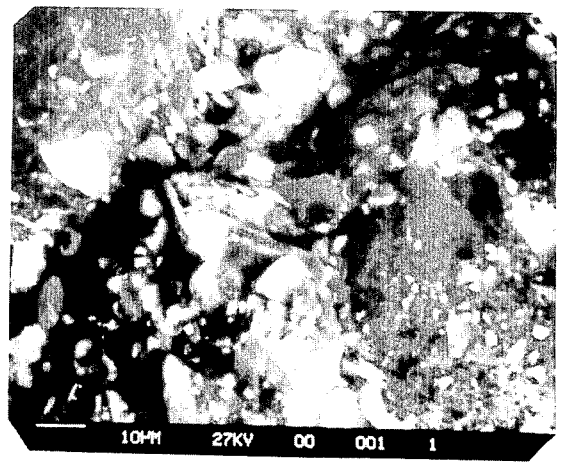
Figure 20:
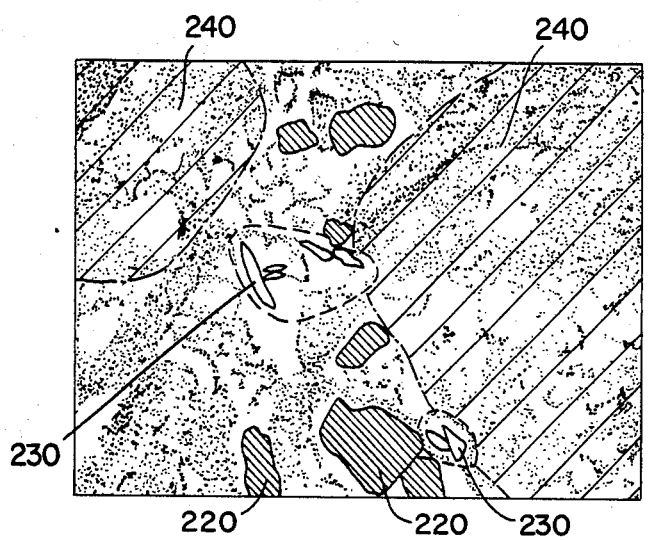
Figure 21:
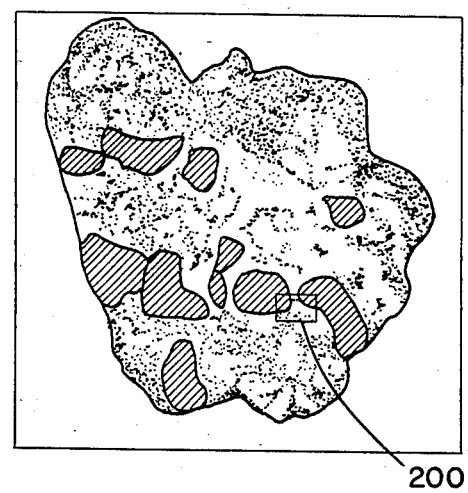

FIGS. 18 and 19 are views of cross-sections of the granule shown at the intersection of the arrows 80 in FIG. 7, FIG. 18 being of the whole cross-section and FIG. 19 of the portion of FIG. 18 marked 200 in FIG. 21 on an enlarged scale;

FIG. 20 is a drawing of FIG. 19; and

Figure 9:
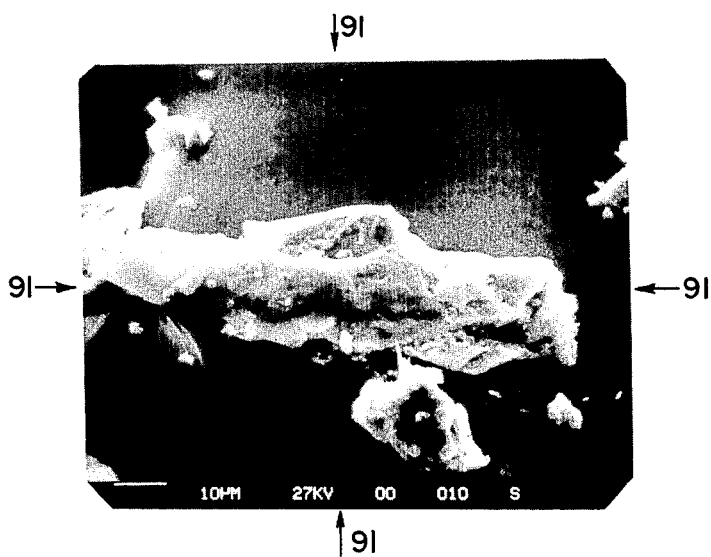
Figure 10:
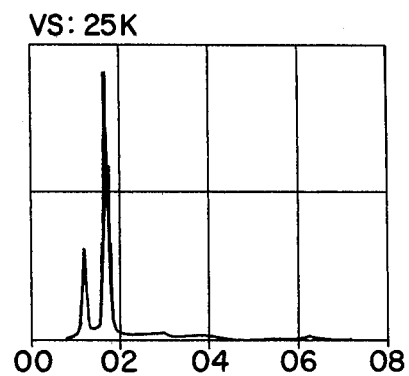
Figure 11:
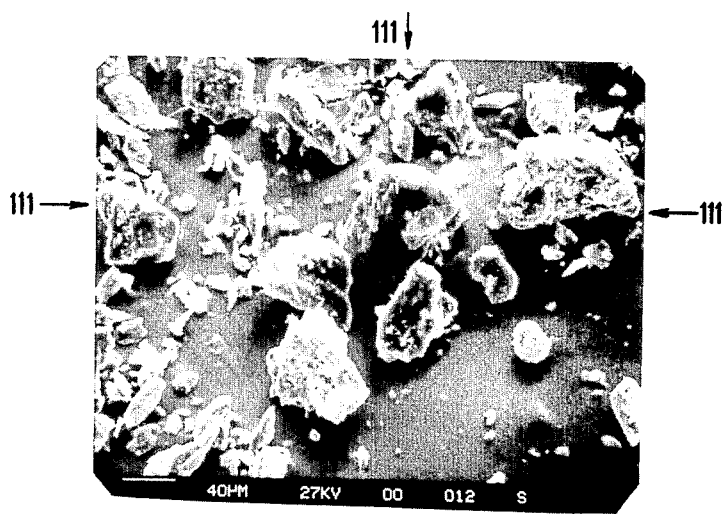
Figure 12:
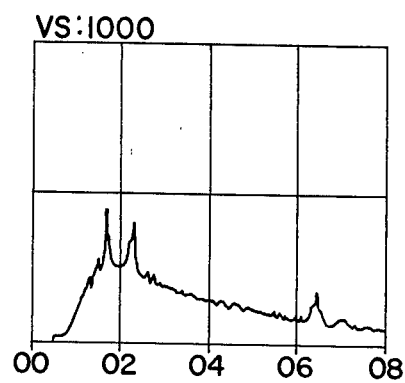
Figure 13:
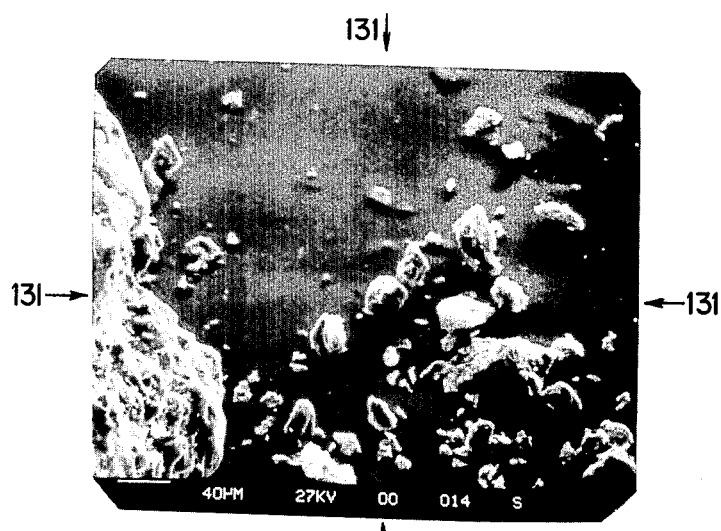
Figure 22:
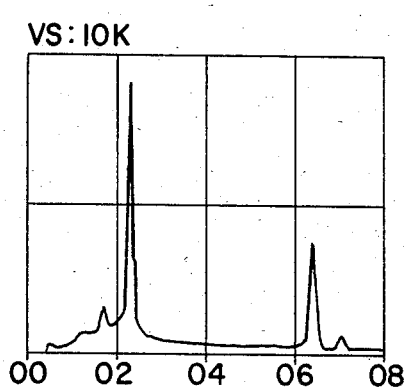
Figure 23:
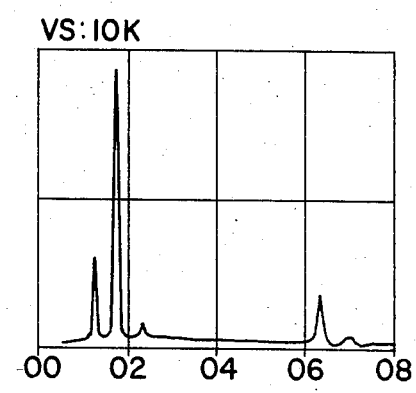
Figure 24:
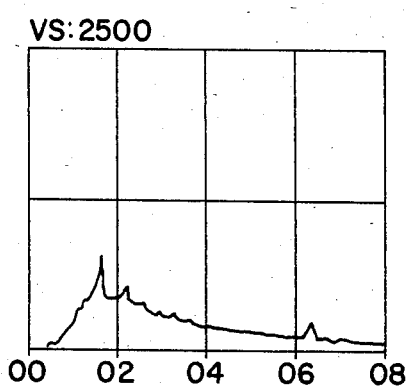
Figure 25:
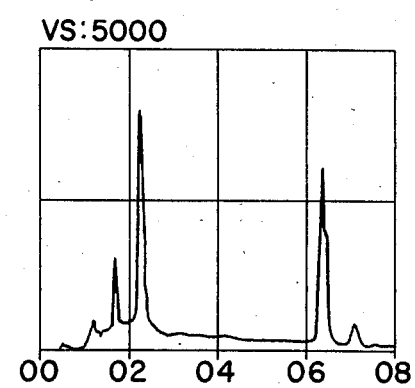

FIG. 21 is a drawing of FIG. 18;

FIG. 22 is an EDAX plot carried out at the sites marked 220 in FIG. 20 which by comparison with FIG. 4 are revealed to be essentially pure iron sulphate;

FIG. 23 is an EDAX plot carried out at the sites marked 230 in FIG. 20 which by comparison with FIG. 9 are revealed to be very largely talc with slight traces of iron sulphate;

FIG. 24 is an EDAX plot carried out at the sites marked 240 in FIG. 20 which by comparison with FIG. 2 are revealed to be essentially pure lactose with only very slight traces of iron sulphate; and FIG. 25 is an EDAX plot of the whole area of FIG. 19.

Each photomicrograph carries a scale on it indicating the magnification. The samples were made by adhering to the stub of the electron microscope sample carrier, the powder in question, by means of a graphite adhesive following which the samples were graphite coated under vacuum so that the graphite would discharge to earth the stream of electrons directed at the sample during the electron microscopy process. The EDAX plots were X-ray emission analyses during the photomicrographic process.

The EDAX plots are bar charts of electron volt values versus X-ray count at each electron volt value and is a cumulative count over 100 seconds. The vertical scales (VS) vary in the different plots and their values are given.

In each plot the small peak at 1.8 eV may be due to silicon components in the electron scanning apparatus.

FIG. 1 is pure lactose. The semi gaussian curve of FIG. 2 is observed to be typical of organic compounds containing carbon, hydrogen and oxygen and provides a finger print for FIG. 24.

Figure 14:
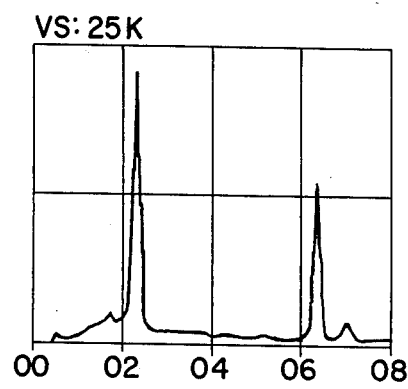

FIG. 3 ia pure ferrous sulphate. The sulphur peaks $K_\alpha$ and $K_\beta$ at 2.3 and 2.4 eV are combined and the iron peaks $K_\alpha$ and $K_\beta$ are at 6.4 and 7.1 eV. This provides a finger print for FIGS. 14 and 22.

FIG. 9 is pure talc. The silicon peak $K_\alpha$ is at 1.8 eV and the magnesium peak $K_\alpha$ is at 1.3 eV. This provides a finger print for FIG. 23.

EXAMPLE 1

25.75 kilograms of ferrous sulphate (British Pharmacopiea grade dried at 40° C.) (of particle size distribution as shown in Table 1A) was mixed with 20.66 kilograms of lactose monohydrate (of particle size distribution shown in Table 1B) and 5.15 kilograms of Eudragit RSPM resin (particle size shown in Table 1A) were blended in a heavy duty Z blade mixer which was sealed from the atmosphere during mixing for the 5 minute mixing period.

Prior to this mixing procedure the dried ferrous sulphate was passed through a mill fitted with a suitable screen (of nominal aperture 550 microns) to separate the primary particles from the agglomerates with minimal comminution. The Lactose and Eudragit RSPM were seived through a 30 mesh screen (apertures 590 microns). The ferrous sulphate had previously been milled to produce the particle size distribution given in Table 1A.

Coulter counter analysis was done in a 4% ammonium thiocyanate isopropyl alcohol solution saturated with ferrous sulphate and filtered through a 0.8 micron filter membrane. The ferrous sulphate was then mixed as a thick paste in this electrolyte to break down the tough agglomerates to the primary particles.

The paste was then suspended in the electrolyte and a first measurement gave a mean particle size of 19 (+97;−5) microns (m.p.s. is at 50% of particle size versus weight, positive deviation at 16% and negative deviation at 84%).

A repeat measurement gave an m.p.s. of 21 (+63;−5) microns.

Coulter m.p.s. was thus about 20 microns. More broadly materials with Coulter m.p.s. in the range 5 to 40 e.g. 10 to 30 are likely to be usable.

TABLE 1A

| | FeSO4 (milled) | | Eudragit RSPM | |
| --- | --- | --- | --- | --- |
| | 50% | 100 microns | 50% | 56 microns |
| Sieve size (micron)[1] | % under-size | % retained on | % under-size | % retained on |
| 10 | 3.4% | 96.6% | 3.0% | 97.0% |
| 20 | 16.2% | 83.8% | 10.0% | 90.0% |
| 32 | 30.4% | 69.6% | 44.2% | 55.8% |
| 56 | 35.6% | 64.4% | 50.0% | 50.0% |
| 75 | 38.1% | 61.9% | 64.5% | 35.5% |
| 90 | 40.6% | 59.4% | 72.0% | 28.0% |
| 125 | 70.0% | 30.0% | 85.6% | 14.4% |
| 180 | 98.3% | 1.7% | 96.5% | 3.5% |
| 250 | 100.0% | 0% | 100.0% | 0% |

[1]These were Alpine (Trade Mark) airjet sieve analyses.

TABLE 1B

| | Purified Talc | | Lactose | |
| --- | --- | --- | --- | --- |
| | 50% | 14 microns | 50% | 65 microns |
| Sieve size (micron)[1] | % under-size | % retained on | % under-size | % retained on |
| 10 | 38% | 62% | 3.4% | 96.6% |
| 20 | 67% | 33% | 5.0% | 95.0% |
| 32 | 80.6% | 19.4% | 8.7% | 91.3% |
| 56 | 95.9% | 4.1% | 32.5% | 67.5% |
| 75 | 98.2% | 1.8% | 68.6% | 31.4% |
| 90 | 99.2% | 0.8% | 86.7% | 13.3% |

TABLE 1B-continued

| Sieve size (micron)[1] | Purified Talc | | Lactose | |
|---|---|---|---|---|
| | 50% % under-size | 14 microns % retained on | 50% % under-size | 65 microns % retained on |
| 125 | 100% | 0% | 99.6% | 0.4% |
| 180 | | | 100.0% | 0% |
| 250 | | | | |

[1] These were Alpine (Trade Mark) airjet sieve analyses.

The blended ferrous sulphate, lactose and Eudragit in the Z blade mixer then had from 4.6 to 5.0 liters of industrial methylated spirits (19 vols. 99% w/v ethyl alcohol plus 1 vol. of approved wood naphtha) added whilst mixing over a period of 2 minutes. The industrial methylated spirits is the polymer spreading granulating agent. It is a nonsolvent for all the other ingredients. The wet mixture was then mixed for 10 to 15 minutes without heating and then the jacket of the mixer was heated with hot water at 60° to 70° C. and mixing continued until the mass broke up into granules. The mixture was then discharged from the mixer and whilst this was occurring cooling water was run through the jacket of the mixer. The granulate was then passed through a ⅛ inch band on a milling machine to produce a finer granulate and the material was then dried in a fluidized bed drier first of all for 15 minutes without heating, then for 10 minutes at a 35° C. inlet temperature and a 40° C. exhaust temperature, and then for 10 minutes without heating. The air flow was about 1400 cubic feet per min. (CFM) (39200 liters per minute) through the mass of about 51 kilograms of material. The granules had the particle size distribution shown in Table 2. These granules are free flowing and require no further size reduction. They could therefore be used as a free flowing powder rather than being tableted. One use for such a powder would be as a long acting moss killer for use on lawns.

EXAMPLE 2

However excellent slow release tablets can be made by tableting the granules produced in Example 1. Thus granules from Example 1 (51 kilograms) were blended with 60.96/13 kilograms of purified talc (of particle size as shown in Table 1A) and 3.68/13 kilograms of magnesium stearate, and tableted in conventional manner. The average particle size of the granules was 130 microns and the size distribution is given in Table 2.

TABLE 2

| | GRANULES | | | | |
|---|---|---|---|---|---|
| Sieve size (micron)[1] | % under-size | % retained on | SIEVE SIZE (micron) | % under-size | % retained on |
| 10 | 9% | 91.0% | 355 | 77.0% | 23.0% |
| 20 | 14.4% | 85.6% | 425 | 79.8% | 20.2% |
| 32 | 20.3% | 79.7% | 500 | 84.2% | 15.8% |
| 56 | 28.2% | 71.8% | 760 | 92.9% | 7.1% |
| 75 | 33.5% | 66.5% | 1000 | 99.9% | 0.1% |
| 90 | 37.5% | 62.5% | | | |
| 125 | 48.0% | 52.0% | | | |
| 180 | 60.4% | 39.6% | | | |
| 250 | 68.7% | 31.3% | | | |

The mechanism of the blending and granulation is thought to be that when the ethanol as industrial methylated spirits is added to the blend of dry blended powders the Eudragit RSPM is activated and spreads itself throughout the mass. As the ethanol evaporates the resin is deposited largely at the surface of the granular particles being carried there by the solvent front, the lactose and ferrous sulphate being largely insoluble in ethanol. The lactose particles, being larger than the ferrous sulphate particles, act largely as nuclei for the agglomeration of the small primary particles of ferrous sulphate and lactose the whole being bound together at the granule level by a film of Eudragit RSPM resin. The resultant granules from fluid bed drying are free-flowing and the passage through a coarse screen using knives rather than hammers in the milling operation is merely to remove large agglomerates. The talc and magnesium stearate are added to the mixture prior to tableting, the former as a physiologically inert, insoluble filler in proportion to the resin to prevent caking on standing and to extend the matrix resin on compression (at the granule surface) and to prevent caking on standing and the magnesium stearate as a conventional die-wall lubricant. It will be appreciated that both these excipients are insoluble. The granulated resin particles which it will be appreciated are permeable under the conditions in the intestine were tableted by compression on a conventional rotary tablet machine and during this compression process the resin coated granules fuse together and form a continuous sponge-like matrix.

The granules may be compressed as a conventional tablet alone, or co-compressed as a layered tablet with other active principles in the other layer (layering in this context including dry coating by either granule stock or conventional layering one on top of the other). The tablets may be film coated if so desired.

The ferrous sulphate, the solute, is an active ingredient that is relatively insoluble in water and has a narrow pH band absorption window in-vivo. It has a binodal particle size distribution with a significant proportion of primary particles of less than 50 microns and preferably less than 30 microns. It is insoluble in the granulation solvent.

The lactose, the solute extender, is an agent that has a good water solubility, it is soluble in 6 parts of water (BP), and is of a specific narrow particle size distribution to assist the granulation process (especially in the range 60 to 80 microns). It effectively transports the active ingredient out of the channels of the matrix independent of pH (or dissolved oxygen level).

This agent is also insoluble in the granulation solvent.

The matrix plastic is a polyacrylate resin of limited permeability which on processing and development combines with the talc, the matrix extends to form an insoluble skeleton or "sponge-like" matrix, the solute and solute extender is the combined state making up the "channels" in the sponge-like matrix.

The talc is the matrix extender and is a water insoluble, granulation solvent insoluble, mineral acid insoluble agent, used to extend and support the matrix plastic in the dosage form (the skeleton). It may be that by acting as a carrier for the polyacrylate it increases the latter's effectiveness and reduces the amount required for matrix formation.

The selected starting material particle sizes also ensure that the granules resulting from the combining of the solute, solute extender and matrix plastic in the mixing, massing and drying process, are free flowing and require no further size reduction.

Figure 15:
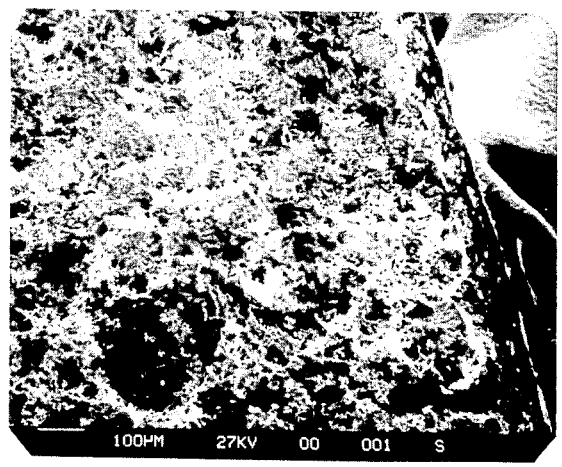
FIG. 15 is a cross-section of a tablet made by compression alone of the granules shown in FIGS. 5, 6 and 7, the cross-section being prepared with a sharp razor.
Figure 16:
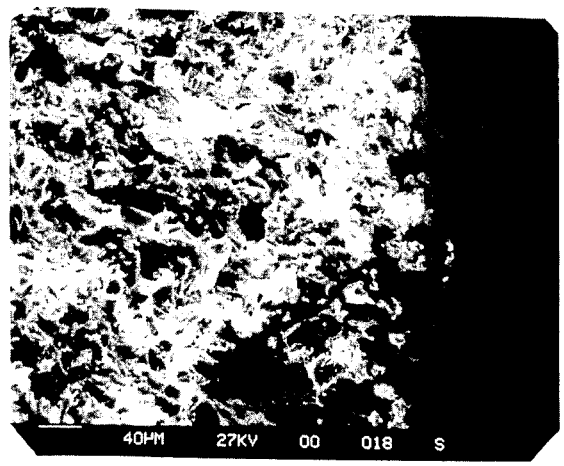
FIG. 16 is a view similar to FIG. 15 but prepared by breaking the tablet.
Figure 17:
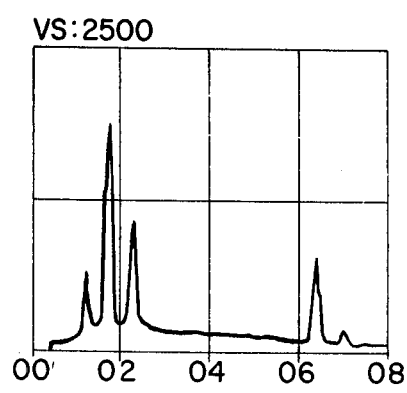
FIG. 17 is an EDAX plot carried out on the region shown in FIG. 16.

FIGS. 15 and 16 are views of a cross-section of this continuous sponge-like matrix formed by tableting the granules and show the continuous three-dimensional matrix of the compressed particles.

X-ray emission analysis (EDAX) of the tablet as were described for the resin particles gave the same qualitative identification of the composition.

Figure 5:
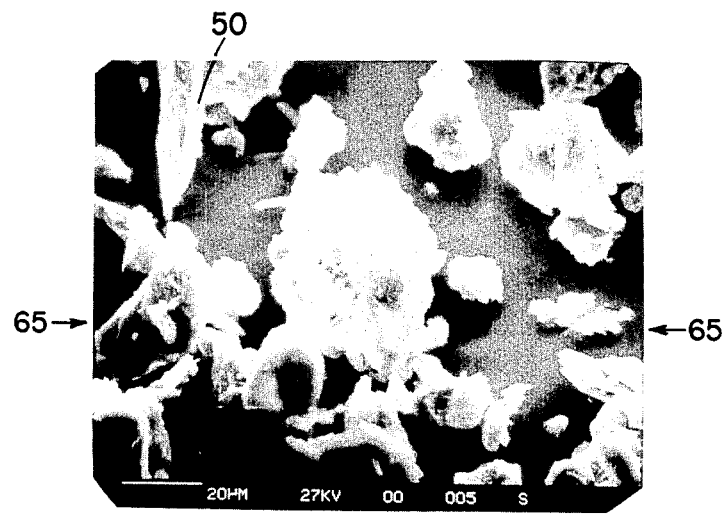
Figure 6:
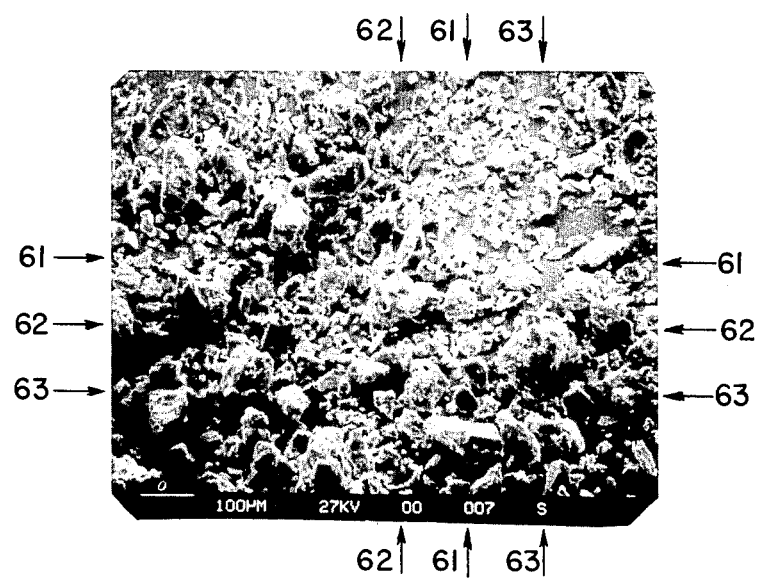

It will be observed that the individual granules shown in FIGS. 5, 6 and 7 can no longer be detected in the continuous three-dimensional matrix of material shown in the tablet.

Delayed release or controlled release pharmaceutical formulations are known in which the active ingredient is located within a porous resin coating but these materials will not have the benefits of the present tablet formulation in that they will not have a continuous rate of release of the active ingredient because once the active ingredient inside the coating has become significantly dissolved there will be nothing to support the coating and it will tend to collapse inwards or rupture outwardly either of which events will cause the rate of release to suddenly change markedly. Thus in the event of inward collapse the rate at which the active material is released by the formulation will be reduced, whilst in the event of rupture of the film wall the rate of release will increase.

With the present invention a substantially constant surface area for dissolution will be exposed throughout because the continuous matrix in the tablet and thus its porous structure will remain substantially constant and the active material being distributed substantially evenly throughout the matrix will remain evenly accessible to the solubilizing liquids throughout the dissolution process.

When large granules in accordance with the invention were separated from the blend shown in FIG. 7, by shaking to segregate them, and placed in tap water at 20° C. for 24 hours they lost iron content as was apparent by the water turning yellow orange (ferric hydroxide) but on drying had not increased or decreased in size.

When tablets made from such granules were placed in tap water under the same conditions they kept their shape for 3 hours but had broken down to small fragments after 18 hours though some of these fragment were significantly larger than the original granules.

Eudragit polyacrylate material is preferred and is insoluble in water, alkaline and acid environments and is poorly permeable to water. The talc is used as an insoluble support and extender and the poorly permeable plastic matrix contains the active ingredient and the active ingredient is extended with a soluble excipient namely the lactose in this instance which, as described above, has a controlled particle size relationship to the active ingredient. The active ingredient and the extender are located within what are in effect channels in the matrix and release by dissolution occurs in a controlled manner less dependent upon the pH of the environment than in prior controlled release formulations. Typical tablet proportions in milligrams of ingredient per tablet will be the equivalent of 150 milligrams of dried ferrous sulphate, 120.35 milligrams of lactose, 30 milligrams of Eudragit RSPM, 30 milligrams of purified talc, and 1.65 milligrams of magnesium stearate. The industrial methylated spirit is substantially entirely removed during the processing of the granules which are then convertable by pressure alone to tablets.

EXAMPLES 3 AND 4

Examples 1 and 2 were repeated using 45.18% of dried ferrous sulphate as the active ingredient or solute, 36.25% of lactose as the water soluble extender or solute extender, 9.04% of Eudragit RSPM as the polymer film matrix or matrix plastic, 9.04% of purified talc as the matrix extender with 0.5% of magnesium stearate as lubricant. The ratio of solute to solute extender is thus 5:4, to matrix plastic 5:1 and to matrix extender 5:1. The ratio of matrix plastic to matrix extender is 1:1.

Whilst Eudragit is extremely convenient and is preferred other resins having similar physiological and pharmaceutical compatability and of necessary insolubility such as perspex polyacrylate, methyl acrylate, methyl methacrylate and copolymers thereof, or other pharmacologically acceptable film-forming solvent, e.g. ethanol, soluble, water-insoluble materials such as polyvinyl esters, polyvinyl acetals, polyvinyl chloride, butadienestyrene copolymers and polyacrylic esters could be used. The Eudragit resins are copolymers based on acrylic acid and methacrylic acid esters having a low content of quaternary ammonium groups. The mean molecular weight of the RSPM grade is approximately 150000 and the powder as used already contains 0.5% talc as an anticaking agent that is in addition to the talc added as described in the process above.

Whilst the extending solvent referred to has been described as ethanol it will be appreciated that the resin can be one soluble in other solvents such as ketones, esters and aromatic or chlorinated hydrocarbons but obviously from a pharmacalogical acceptability point of view such solvents are less prudent than materials such as ethanol. Obviously if the controlled release function is to be achieved the polymers must be capable of being resistant to any significant attack within the human digestive system which might be such as to break down their structures within the period in which it is intended that release of the active ingredient should be controlled and thus in general they will be resistant to acid and alkaline environments.

Whilst talc has been described as an extender in an amount of 1:1 in proportion to the Eudragit RSPM on a weight basis in the above formulation, other fillers which are practically insoluble in water and in mineral acids of pharmaceutically acceptable type such as kaolin, calcium sulphate, calcium phosphate dibasic or fine particle size silicic acid or silicates could be used, talc has however been found to be particularly satisfactory. Lactose monohydrate has been described as the preferred water soluble (ethanol insoluble) material but any water soluble material again of pharmaceutically acceptable type e.g. soluble in less than 10 parts of water (BP) and which can be readily obtained in the desired particle size range and particle size distribution to match that of the active ingredient can be used and such materials may be drawn from such water soluble materials as salts, other sugars, polyethyleneglycols, polyvinylpyrrolidones, and polyvinyl alcohols provided that it in turn is relatively insoluble in the extending solvent selected for the process. Examples of such materials are of the salts, sodium chloride, of the sugars, saccharose, glucose, sorbitol and mannitol, of the polyethyleneglycols, polyethyleneglycols of molecular weights up to 20,000, of the polyvinylpyrrolidones that known as Kollidon 25 from BASF and of the polyvinylalcohols that known as Mowiol N 30-98 from Hoechst. The poor permeability of the Eudragit resin also helps to maintain the ferrous sulphate in a stable ferrous state and to inhibit its conversion to the ferric state i.e. it maintains the active ingredient in its pharmacologically active form for a longer period than would be the case if for example the resin was more permeable to water or acids or alkalies.

Whilst the invention is described with particular reference to ferrous sulphate as the active ingredient it will be appreciated that it will be applicable to many other active ingredients, such as pharmaceutical compounds, herbicides, insecticides, fertilizers and also compounds used in veterinary practice, which can be reduced to fine particle size and whose particle size can be related as prescribed herein by milling or other fractionating to that of the water soluble extender.

What we claim as our invention and desire to secure by Letters Patent is:

1. A granular composition having particles of average particle size as determined by sieving in the range 70 to 500 microns the said particles comprising up to 55% of active ingredient having primary particles the maximum dimension (A) of which as determined by microscopy is less than 50 microns and a particulate water soluble extender having an average particle size (B) as determined by sieving in excess of 50 microns, the particles of active ingredient and water soluble extender being held in self-supporting spaced relationship by a water insoluble polymer film matrix providing the balance of the weight of the particle and being less than 50% by weight of the particle.

2. A granular composition as claimed in claim 1 in which the particles are of average particle size in the range 75 to 250 microns.

3. A granular composition as claimed in claim 1 in which the fine primary particles of the active ingredient have a maximum dimension (A) below 40 microns.

4. A granular composition as claimed in claim 1 in which the water soluble extender has an average particle size (B) in the range 50 to 100 microns.

5. A granular composition as claimed in claim 1 in which the ratio of B:A is in excess of 1:1.

6. A granular composition as claimed in claim 1 in which the ratio of B:A is in excess of 2:1.

7. A granular composition as claimed in claim 1 in which in the particles 45 to 55% is the active ingredient, 40 to 50% is the water soluble particulate extender and less than 15% is the polymer film matrix.

8. A granular composition as claimed in claim 1 in which the active ingredient is ferrous sulphate, the water soluble extender is lactose and the polymer is a polyacrylate polymer.

9. A blend convertible by pressure alone to a substantially continuous three-dimensional porous matrix substantially devoid of separate resin particles, comprising active ingredient/water soluble extender/resin particles as defined in any one of claims 1 to 8 in which the active ingredient comprises 45 to 60% by weight, the water soluble extender comprises 35 to 45% by weight, and the resin comprises 5 to 15% by weight and a water insoluble extending agent or filler for the matrix resin and a water soluble or insoluble tableting aid or lubricant, the active ingredient/water soluble extender/resin particles comprisinig 80 to 95% by weight, the water insoluble extending agent or filler for the matrix resin comprising 5 to 15% by weight and the water soluble or insoluble tableting aid or lubricant comprising 0.2 to 5% by weight of the blend.

10. A process for forming a slow release tablet which comprises converting a blend in accordance with claim 9 by pressure alone without the aid of a solvent to tablet form.

11. Slow release tablets whenever made by a method as claimed in claim 10.

12. Slow release capsules incorporating a granular composition as claimed in any one of claims 1 to 8.

* * * * *